Feb. 28, 1933. G. H. PRING Plant Pat. 55
WATER LILY
Filed Sept. 22, 1932
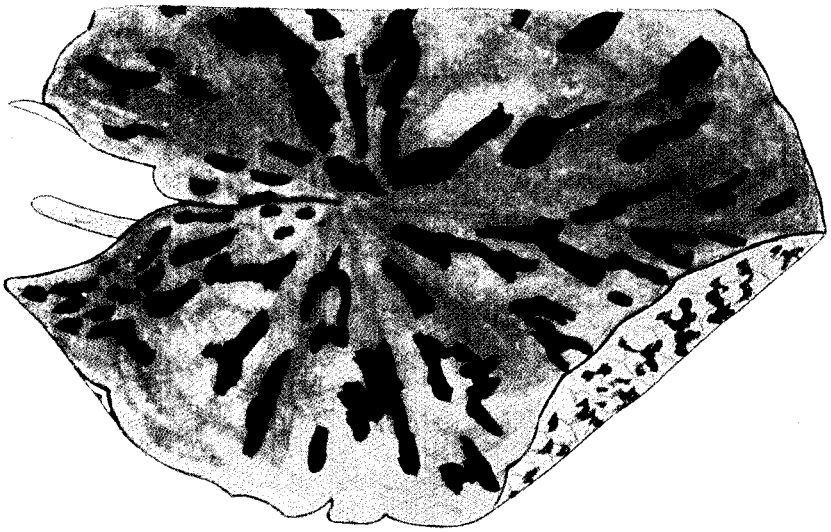
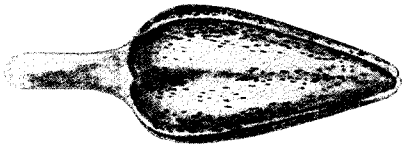
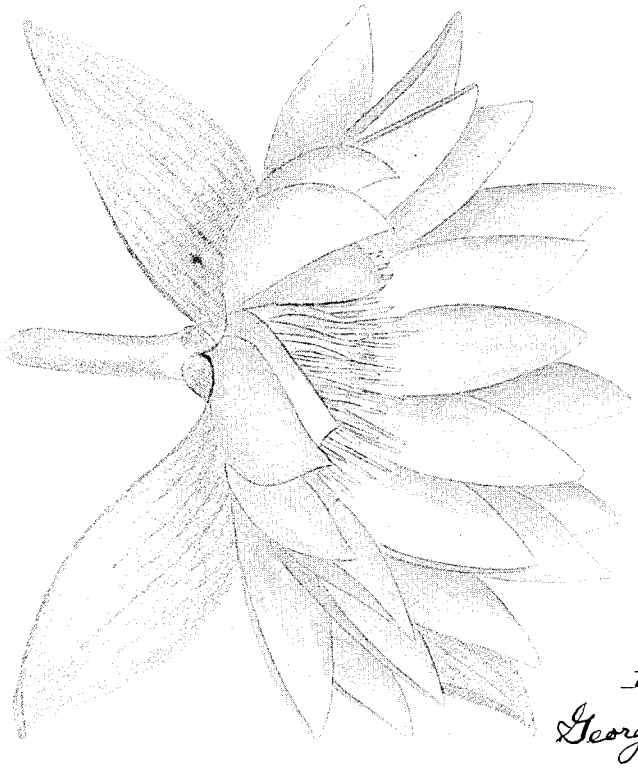
Inventor
George Harry Pring
Orville M. Kile
Plant Patent Agent Patented Feb. 28, 1933 Plant Pat. 55

UNITED STATES PATENT OFFICE

GEORGE HARRY PRING, OF ST. LOUIS, MISSOURI, ASSIGNOR TO THE MISSOURI BOTANICAL GARDEN, OF ST. LOUIS, MISSOURI, A CHARITABLE TRUST OF MISSOURI

WATER LILY

Application filed September 22, 1932. Serial No. 634,427.

My new variety of water lily, or nymphæa, belongs to the class known as tropical day-blooming. It was developed by me as the result of definite and extensive breeding. Its parentage is as follows:

Nymphæa capensis X N. capensis } N. castaliiflora X N. ovalifolia } N. "Mrs. Edwards Whitaker" X N. ovalifolia } N. "Mrs. George H. Pring" X N. stuhlmannii } N. my new variety The first blossoms of this plant were produced in 1931. It has since been reproduced asexually—from bulbs—and has not been offered for sale to the public.

The purpose of my invention is to provide a tropical day-blooming water lily of yellow color. This is the first tropical day-blooming water lily known that has yellow blossoms; heretofore the only known colors were white and various shades of pink and blue.

The accompanying illustration shows in full color a fully opened flower, a bud with stem attached, and a leaf.

The following is a detailed description of this new variety of tropical day-blooming water lily:

*Leaves and stems.*—Leaves of submerged seedlings, green triangular ovate with acute lobes, primary floating leaves ovate orbicular green, marmorated with reddish brown, lighter green on the under side, spotted with purple, sinus open to the center, lobes acute. Mature leaves ovate to orbicular 18 inches long, 15 inches wide, sub-peltate, margins irregularly undulate, pea green above, prominently marmorated with reddish brown, fading with age; lighter green on the under side, faintly spotted with purple; sinuses overlapping about one-third from the center of the leaf, occasionally forming a raised keel, the remaining two-thirds gradually diverging, terminating into acuminate lobes. Petioles terete green attaining a length of six feet when fully developed.

*Flowers.*—Pale viridine yellow (Ridgeway's Color Guide and Nomenclature), 10 to 12 inches across, opening 5 to 6 days from 7 a. m. to 6 p. m. during August. Extremely fragrant; 3 to 6 opening at one time. Bud ovate conical, light green striped with dark purple. Peduncle green, rising 1 to 1½ feet above the water. Cross section shows 8 main air-canals, circled by 16 smaller ones; these again surrounded by smaller air-canals.

*Sepals.*—Four, wedged, ovate-triangular, 4½ inches long, 1¾ inches wide. Prominently hooded at the apex, thick, fleshly in texture. Outer surface green, lighter toward the margins, inner surface pale viridine yellow, greenish yellow at the base, showing 10 to 12 veins.

*Petals.*—30 to 38, comprising 4 whorls. The outermost lanceolate-obtuse, slightly hooded at the apex. 4½ inches long, 1½ inches wide. The outer surface pale viridine yellow, channeled longitudinally with green and thicker in texture along the medial vein. Green at the base, showing 6 to 8 veins. Inner surface pale viridine yellow, inner whorls pale viridine yellow, becoming shorter, narrower, acute to acuminate.

*Stamens and stigma.*—Stamens 190 to 200. Outermost whorl 2 inches long, with appendages ovate-oblong at the base. Linear above, pale lemon yellow, base lemon yellow, pale viridine yellow at the apex. Inner whorls shorter and narrower toward the innermost, which is linear. Carpels 25 to 30 with styles oblong, obtuse, pale viridine yellow. Stigma slightly concave, exposed the first day by a corona of closely packed, perpendicular stamens. Only receptive the first day of opening. The second day the introrse inner whorls of stamens cover the stigma. The fourth day the stamens become extrorse exposing the nectarless stigma.

*Fruit.*—Globose, 2 to 3 inches in diameter. Contains numerous fertile seeds.

What I claim as new is:

The variety of tropical day-blooming water lily herein shown and described, characterized particularly by the yellow color of its blossoms.

In testimony whereof I affix my signature.

GEORGE HARRY PRING.